(12) United States Patent
Yamamoto et al.

(10) Patent No.: US 7,090,671 B2
(45) Date of Patent: Aug. 15, 2006

(54) LASER CORNEAL SURGERY APPARATUS

(75) Inventors: Tetsuya Yamamoto, Gamagori (JP); Hirokatsu Makino, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/123,482

(22) Filed: Apr. 17, 2002

(65) Prior Publication Data
US 2002/0156468 A1 Oct. 24, 2002

(30) Foreign Application Priority Data
Apr. 20, 2001 (JP) .............................. 2001-122409

(51) Int. Cl.
*A61F 9/08* (2006.01)
(52) U.S. Cl. ................ 606/12; 606/5; 606/10
(58) Field of Classification Search .............. 606/5, 606/10–12
See application file for complete search history.

(56) References Cited

U.S. PATENT DOCUMENTS 4,911,711 A * 3/1990 Telfair et al. ................... 606/5
5,507,799 A 4/1996 Sumiya
5,637,109 A 6/1997 Sumiya
6,817,998 B1 * 11/2004 LaHaye ....................... 606/11

FOREIGN PATENT DOCUMENTS

| EP | 0 956 840 A2 | 11/1999 |
| JP | A 4-242644 | 8/1992 |
| JP | A 11-342151 | 12/1999 |

\* cited by examiner

*Primary Examiner*—David Shay

(57) ABSTRACT

The present invention intends to provide a laser corneal surgery apparatus in which an optical system for directing and irradiating a laser beam onto a cornea can be protected from water droplets and the like. The laser corneal surgery apparatus for ablating a cornea of a patient's eye by a laser beam comprises an observation optical system for observing the patient's eye, an irradiation optical system for irradiating the laser beam onto the cornea, and a protection plate which is disposed on an irradiation optical path between the cornea and an optical member included in the irradiation optical system and disposed in a position nearest to the cornea, and which is insertable in and removable from the optical path.

7 Claims, 3 Drawing Sheets

LASER CORNEAL SURGERY APPARATUS

BACKGROUND OF THE INVENTION

1. Field of the Invention

The present invention relates to a laser corneal surgery apparatus for ablating a cornea of a patient's eye by a laser beam for the purpose of correcting a refractive error and the like.

2. Description of Related Art

As keratorefractive surgery using an excimer laser beam which is ultraviolet light, laser assisted in-situ keratomileusis (LASIK) is performed, in which a flap is formed by incising the part from an epithelium to a stroma in layered form, the stroma is ablated (removed) by irradiating a laser beam, then the flap is returned.

A corneal incision apparatus called a microkeratome is used for forming a flap. As disclosed in European Patent Application Publication No. 956840 A2 corresponding to Japanese Patent Application Unexamined Publication No. HEI 11-342151, such an apparatus has been known that a corneal pressing member presses the corneal part projecting from an opening of a suction part sucking and being fixed on a corneal surface so that the projecting part is flattened, then a blade is transversely oscillated and moved straight or rotatably moved to incise the epithelium.

When a surgical operator uses the corneal incision apparatus described above, he may confirm operations of a blade drive using a microscope included in the laser corneal ablation apparatus. In this case, since water (physiological saline) is used as a lubricant to the blade, a spray of water forms, whereby water droplets may adhere to an optical member (a mirror or lens) placed nearest to the cornea to be irradiated in the optical system for guiding and irradiating the excimer laser beam onto the cornea. In general, a coating of a mirror reflecting ultraviolet light is water-sensitive, and adhesion of the water droplets affects the laser irradiation. Further, since water is used for preventing the cornea from getting dry during corneal incision, water droplets generated incident to the blade drive of the corneal incision apparatus may adhere to the optical member nearest to the cornea.

SUMMARY OF THE INVENTION

The present invention has been made in view of the above circumstances and has an object to overcome the above problems and to provide a laser corneal surgery apparatus in which an optical system for directing and irradiating a laser beam onto a cornea can be protected from water droplets and the like.

To achieve the objects and in accordance with the purpose of the present invention, as embodied and broadly described herein, a laser corneal surgery apparatus for ablating a cornea of a patient's eye by a laser beam comprises an observation optical system for observing the patient's eye, an irradiation optical system for irradiating the laser beam onto the cornea, and a protection plate which is disposed on an irradiation optical path between the cornea and an optical member included in the irradiation optical system and disposed in a position nearest to the cornea, and which is insertable in and removable from the optical path.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
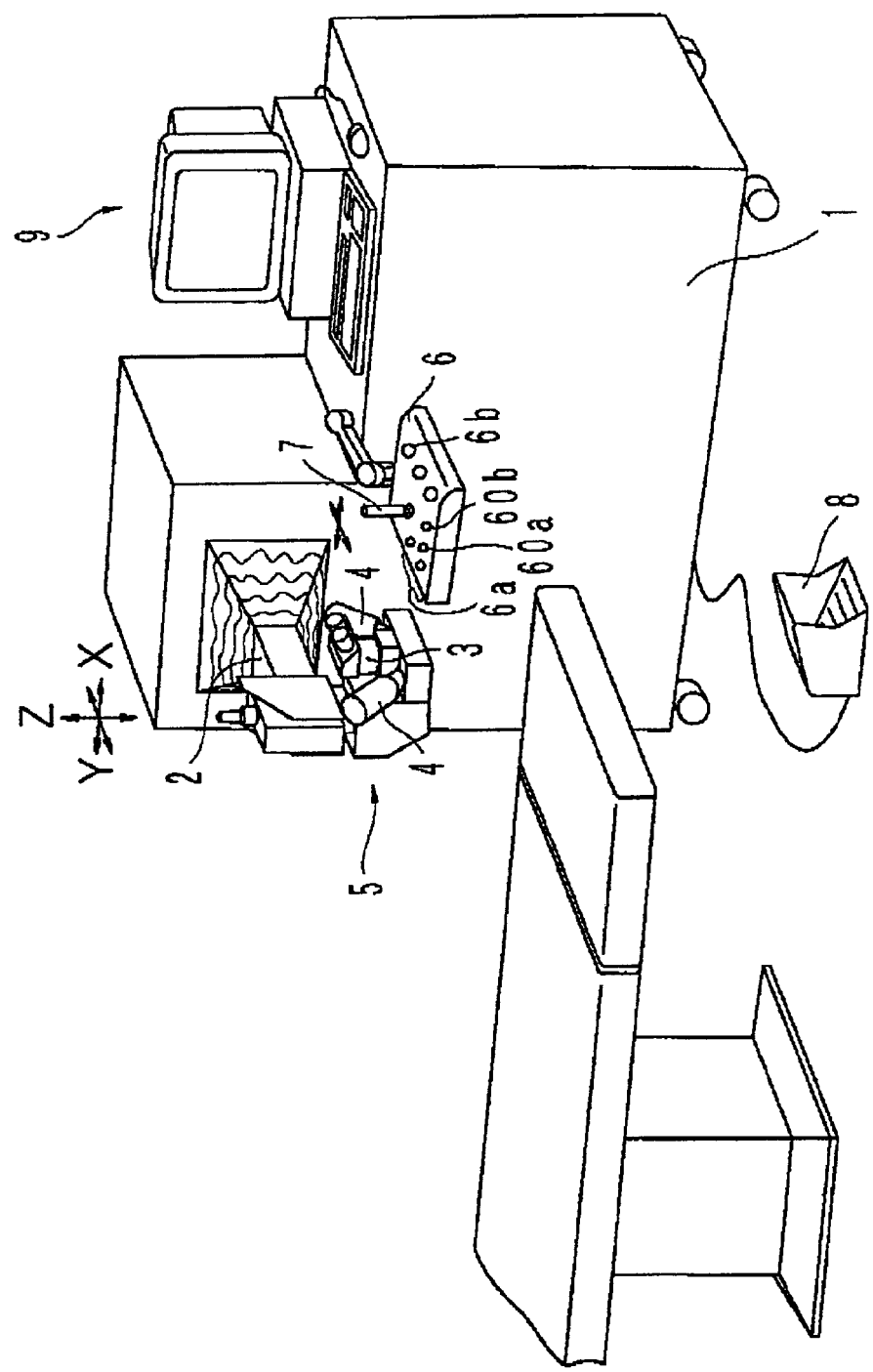
FIG. 1 is an external view of a laser corneal surgery apparatus consistent with the present invention.

A detailed description of one preferred embodiment of a laser corneal surgery apparatus embodying the present invention will now be given referring to the accompanying drawings. FIG. 1 is an external view of the laser corneal surgery apparatus consistent with the present invention.

An excimer laser light source and others are embedded in a main body 1 of the surgical apparatus. An excimer laser beam (hereinafter, it may be also referred to simply as a laser beam) emitted from the excimer laser light source is directed to an arm unit 2 including a laser irradiation (beam directing) optical system. The arm unit 2 is moved by a driving device in an X-Y direction shown in FIG. 1, and a tip portion 5 of the arm is moved in a z direction. The tip portion 5 includes a binocular microscope 3 for observing a patient's eye, an illumination unit 4 for observation, and the like.

A controller 6 includes a joystick 7 for giving a signal to move the arm unit 2 in the X-Y direction, a focus adjusting switch 6a for giving a signal to move the tip portion 5 in the Z direction, a Ready switch 6b for allowing laser irradiation, and the like. Further, the controller 6 includes indicators 60a and 60b such as lamps informing whether a protection plate 40 which will be described below is inserted in an opening (outlet) for emitting the laser beam, or not. A footswitch 8 is disposed to give a laser irradiation signal (a trigger singal). A computer 9 is used to input data about conditions necessary for surgery, as well as to calculate, display, and store laser irradiation control data, and the like.

Figure 2:
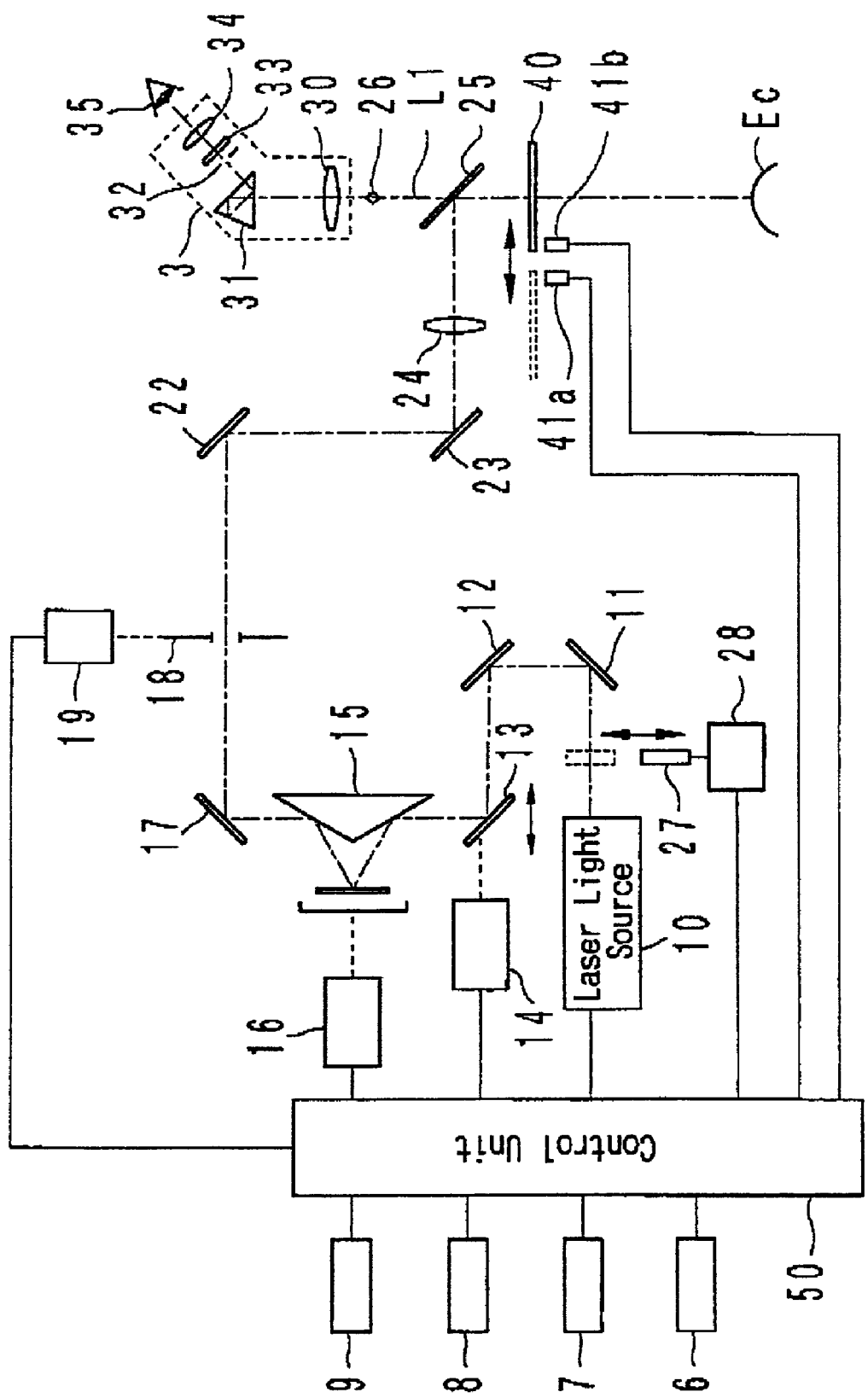
FIG. 2 is a view showing a schematic configuration of optical and control systems of the present surgery apparatus.

FIG. 2 is a view showing a schematic configuration of optical and control systems of the present surgery apparatus. An excimer laser light source 10 emits an excimer laser beam (193 nm) The laser beam emitted from the laser light source 10 is reflected on mirrors 11 and 12, and further reflected on a plane mirror 13. The mirror 13 is moved by a driving unit 14 in a direction of an arrow in FIG. 2 so that the laser beam makes a movement parallel to a direction of the Gaussian distribution, whereby an object can be ablated uniformly. Reference should be made about this point to U.S. Pat. No. 5,507,799 corresponding to Japanese Patent Application Unexamined Publication No. HEI 4-242644 for details.

An image rotator 15 is rotated by a driving unit 16 to rotate the laser beam. Reference numeral 17 is a mirror. A circular aperture 18 of which opening diameter is variable limits an ablation region in circle shape, and a driving unit 19 changes the opening diameter. Reference numerals 22 and 23 are mirrors. A projecting lens 24 projects the aperture 18 on a cornea EC of a patient's eye.

A dichroic mirror 25 has a property of reflecting the excimer laser beam with a wavelength of 193 nm and transmitting the visible light (it may be near-infrared ligh or infrared light)for observation. The dichroic mirror 25 is disposed on an optical axis L1 of an objective lens 30 included in the microscope 3, and it reflects the laser beam toward the cornea Ec. The optical members described above constitute the laser irradiation optical system for directing and irradiating the laser beam onto the cornea Ec. It should be noted that in this laser irradiation optical system, an aiming light source (not illustrated) is provided so that aiming light emitted therefrom is made to be coaxial with the laser beam, and the aiming light is partially reflected on the dichroic mirror 25 to be directed and irradiated onto the cornea Ec.

The microscope 3 for observing the patient's eye is provided above the dichroic mirror 25 An observation optical system disposed in the microscope 3 includes an objective lens 30, an angle deviation prism 31, a diaphragm 32, a reticle 33, and an eyepiece 34, and the constituent elements from 31 to 34 are provided on both binocular optical paths. Reference numeral 35 indicates a surgical operator's eye. An eye fixation light 26 is disposed on the optical axis L1 of the objective lens 30.

The flat protection plate 40 which is insertable and removable is provided on the optical path below the dichroic mirror 25, and it is made of transparent glass transmitting observation light. The plate 40 is preferably disposed as it is inclined with respect to the optical axis L1 of the objective lens 30. The inclination should be set so that reflected light of the fixation light and the aiming light does not enter an observation view of the observation optical system. Photosensors 41a and 41b detect whether the plate 40 is inserted in or removed from the optical path.

A shutter 27 shuts the laser beam from the laser light source 10, and it is removed from the optical path when laser irradiation is permitted. A driving unit 28 drives the shutter 27. A control unit 50 controls the laser light source 10, each of the driving units, and the like, and it connects to the computer 9, the controller 6, the footswitch 8, the photosensors 41a and 41b, and the like.

Figure 3:
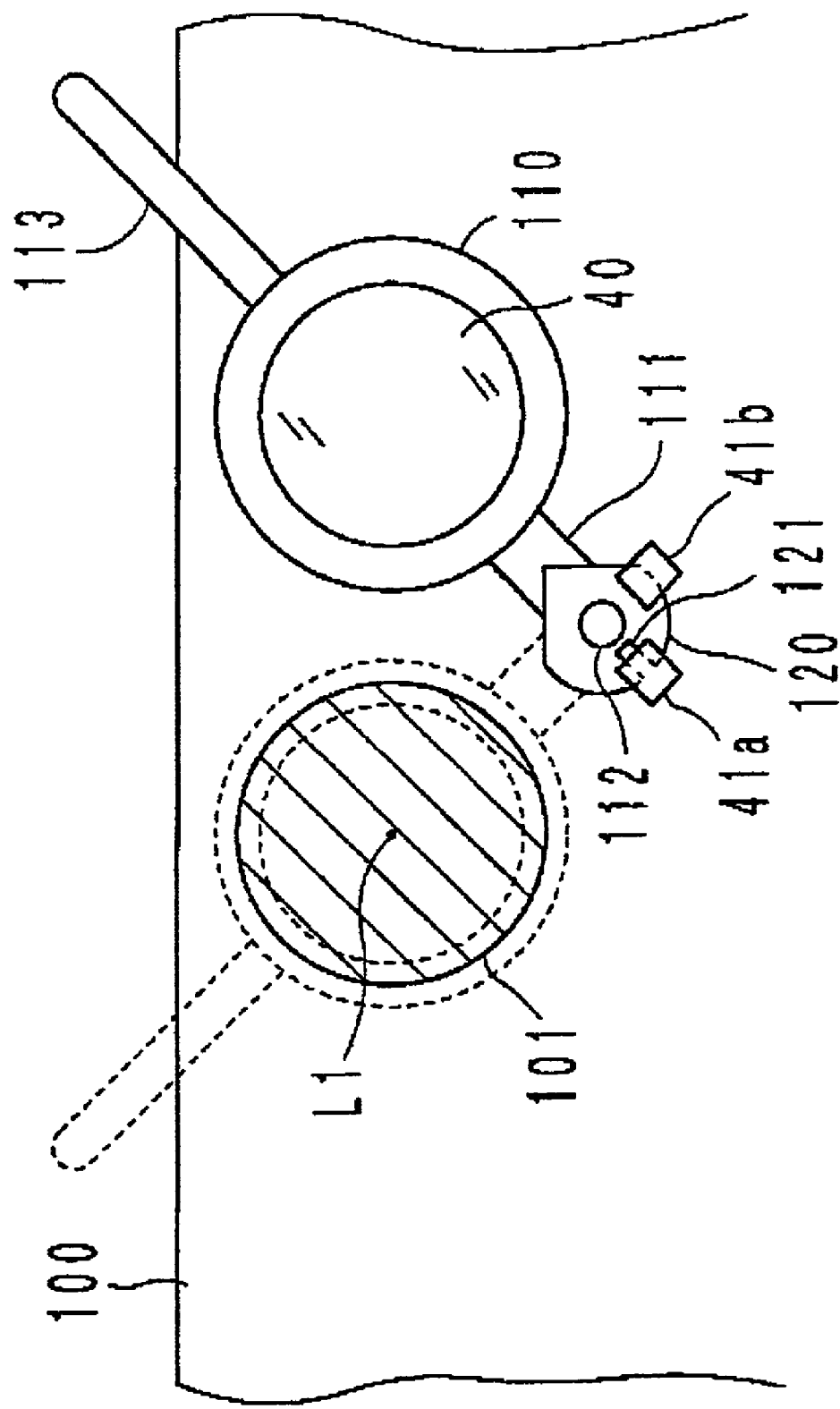
FIG. 3 is a view showing an inserting and removing mechanism of a protection plate.

FIG. 3 is a view showing an inserting and removing mechanism of the plate 40. A bottom plate 100 is disposed at the bottom of the tip portion 5. An opening (outlet) 101 of which center is positioned at the optical axis L1 of the objective lens 30 is formed on the bottom plate 100. The dichroic mirror 25 is disposed above this opening 101, and the laser beam is directed and irradiated through the opening 101. The plate 40 is held by a ring-shaped holding member 110 of which opening diameter is smaller than that of the opening 101. A base part 111 of the holding member 110 is axially supported by a bearing (not illustrated) to be pivotally movable about a pivot 112. A lever 113 is attached to the holding member 110, and operating this lever 113 allows the plate 40 to be shifted about the pivot 112 between a retreat position shown by a solid line and an insertion position shown by the dotted line. Incidentally, a click mechanism constituted of a plunger and the like makes position determination for each of the retreat and insertion positions and gives a tactile feel of click when the lever 113 is operated.

Further, a sensor plate 120 which pivotally rotates about the pivot 112 is attached to the base part 111, and the sensors 41a and 41b detect a notch 121 of the sensor plate 120 pivotally moved with a movement of the plate 40. The sensor 41a's detection of the notch 121 indicates that the plate 40 is in the specified retreat position. The sensor 41b's detection of the notch 121 indicates that the plate 40 is in the specified insertion position.

The operations of the apparatus having the above structure will be described. In the case where the corneal incision apparatus disclosed in European Patent Application Publication No. 956840 A2 corresponding to Japanese Patent Application Unexamined Publication No. HEI 11-342151 is used prior to irradiating the laser beam, the surgical operator manipulates the lever 113 to insert the plate 40 in the opening 101. The sensor 41b detects an insertion state of the plate 40. The control unit 50 lights the indicator 60a of the controller 6 upon receiving a detection signal from the sensor 41b to notify that the plate 40 is inserted in the opening 101. Further, the plate 40 does not obstruct observation using the microscope 3 since it transmits the observation light.

When the surgical operator confirms the operations of the corneal incision apparatus while he observes using the microscope 3, the water used as a lubricant for a blade scatters. At this point, since the plate 40 is inserted in the opening 101 disposed below the dichroic mirror 25, water droplets scattered do not adhere to the dichroic mirror 25, and the mirror 25 is protected. In addition, during incision to form a flap on the cornea Ec the plate 40 remains in the opening 101. In the same manner, this can prevent droplets of water from adhering to the dichroic mirror 25 even when water given to the cornea Ec scatters. Incidentally, disposing the plate 40 to be inclined to the optical axis L1 can prevent the reflected light of the fixation light 30 and the aiming light from entering the observation view of the microscope 3 due to inserting the plate 40.

When the laser beam is irradiated onto the cornea Ec, the surgical operator manipulates the lever 113 to remove the plate 40 from the opening 101 so that the plate 40 is placed in the retreat position. The sensor 41a detects that the plate 40 is placed therein. This time, the control unit 50 lights the indicator 60b upon receiving the detection signal form the sensor 41a to notify that the plate 40 is placed in the retreat position. The surgical operator inputs the data about the conditions for surgery using the computer 9 for necessary preparation and turns the Ready switch 6b on so that the laser can be irradiated. When the foot switch 8 is pushed down, the control unit 50 removes the shutter 27 from the irradiation optical path of the laser beam and controls the drive of the laser light source 10, the movement of the mirror 13, the opening diameter of the aperture 1E, and the like in accordance with a control program. The laser beam from the laser light source 10 is directed to the dichroic mirror 25 and is reflected thereon to be directed and irradiated onto the cornea Ec.

In such a corneal surgery by the laser beam, when the plate 40 is not placed in the retreat position, the laser irradiation cannot be carried out even if the Ready switch 6b is turned on. When the Ready switch 6b is turned on without an input of the detection signal from 41a, the control unit 50 displays an error message on the monitor of the computer 9 (an audio message may be given). Further, when the foot switch 8 is pushed down in this condition, the control unit 50 does not drive the laser light source 10 and keeps the shutter 27 closed to prohibit (stop) the laser irradiation, In the above description, the plate 40 is manually inserted and removed, but it may be electrically driven using a motor. In this case, the plate 40 can be moved by turning the Ready switch 6b on and off. When the Ready switch 6b is turned on, the control unit 50 drives the motor to move the plate 40 placed in the insertion position of the opening 101 to the retreat position. Further, when the Ready switch 6b is turned off (i.e. a ready state is cleared), the plate 40 placed in the retreat position is returned to the insertion position. Since the plate 40 remains in the insertion position when the apparatus is not brought in the ready state, the dichroic mirror 25 can be protected from the water scattered when the corneal incision apparatus is used.

In addition, in the above description, the controller 6 includes the indicators 60a and 60b informing whether the plate 40 is inserted in or removed from the optical path, but these indicators may be disposed within the observation view of the microscope 3. For example, they may be disposed in the position of the reticle 33. This allows the surgical operator to confirm using the microscope 3 whether the plate 40 is in the insertion position of the irradiation optical path or in the retreat position, thereby enhancing usability. That is, at the time of using the corneal incision apparatus, the light of the indicator 60a can help the surgical operator confirm whether the plate 40 has been inserted or not.

Further, as a means of confirming using the microscope 3 that the plate 40 is inserted or removed, the opening diameter of the holding member 110 may be prepared to be smaller than a view observable using the diaphragm 32 of the microscope 3. When the plate 40 is inserted, a shadow of the holding member 110 is observed, and the observation condition differs from the condition in which the plate 40 is placed in the retreat position, thereby informing whether the plate 40 is in the insertion position or not. It may be preferable that a rim of the plate 40 which does not obstruct the observation region at the center be a filter colored in green or the like.

In the above embodiment, the optical member of the laser irradiation optical system protected by the plate 40 is the dichroic mirror placed on the observation optical path, but the optical member may be a mirror placed in a position which is on the optical axis L1 of the objective lens 30 and off the right and left observation optical paths. In this case, if the plate 40 is placed right below the mirror (between the mirror and the cornea Ec), the plate 40 should not necessarily transmit the observation light. Further, the laser irradiation optical system may be configured in such a manner that the excimer laser beam is ultimately irradiated onto the cornea Ec via a condenser lens. In this case, the plate 40 can also protect the condenser lens.

Further, at least one of the sensors 41a and 41b should be provided with the apparatus (preferably, 41b). In this case, the apparatus may include at least one indicator.

Furthermore, in the present embodiment, the optical axis of the laser irradiation optical system is coaxial with the optical axis L1 of the objective lens 30, but they may not be necessarily coaxial as long as they have a predetermined positional relationship.

As described above, according to the present invention, an optical system directing a laser beam to a patient's eye can be protected from water droplets and the like.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser corneal surgery apparatus for ablating a cornea of a patient's eye by a laser beam, comprising:
    a body having an opening;
    an observation optical system for observing the patient's eye;
    an irradiation optical system which is disposed in the body, for irradiating the laser beam onto the cornea through the opening;
    a movable protection plate for preventing water from adhering to an optical member which is included in the irradiation optical system and disposed at a position located nearest to the opening;
    an inserting and removing mechanism unit that inserts the protection plate into the opening when the water is used on the patient's eye and removes the protection plate from the opening when the laser beam is irradiated onto the cornea;
    a sensor that detects whether the protection plate is removed from the opening or is inserted into the opening; and
    a control unit that controls the irradiation optical system to permit irradiation of the laser beam when the protection plate is removed from the opening based on a result of the detection by the sensor.

2. The laser corneal surgery apparatus according to claim 1, wherein the protection plate has a property of transmitting observation light, and the patient's eye may be observed through the observation optical system, the opening and the protection plate when the water is used on the patient's eye.

3. The laser corneal surgery apparatus according to claim 2,
    wherein the observation optical system includes an objective lens, and
    wherein the protection plate is inserted into the opening so as not to be parallel with and orthogonal to an optical axis of the objective lens.

4. The laser corneal surgery apparatus according to claim 1, further comprising informing means for informing a surgical operator of the result detected by the sensor.

5. The laser corneal surgery apparatus according to claim 1, wherein the inserting and removing mechanism unit includes a lever for moving the protection plate manually.

6. The laser corneal surgery apparatus according to claim 1, wherein the inserting and removing mechanism unit automatically moves the protection plate based on a switch signal.

7. The laser corneal surgery apparatus according to claim 6, wherein the inserting and removing mechanism unit moves the protection plate based on the switch signal by a READY switch for enabling the laser irradiation.

* * * * *